United States Patent [19]

Regnier et al.

[11] Patent Number: 5,506,245
[45] Date of Patent: Apr. 9, 1996

[54] THIAZOLIDINEDIONE COMPOUNDS

[75] Inventors: Gilbert Regnier, Chatenay Malabry; Yves Charton, Sceaux; Jacques Duhault, Croissy Sur Seine; Joseph Espinal, Levallois Perret, all of France

[73] Assignee: ADIR et Compagnie, Courbevoie, France

[21] Appl. No.: 374,970

[22] Filed: Jan. 19, 1995

Related U.S. Application Data

[63] Continuation-in-part of Ser. No. 133,898, Oct. 12, 1993, abandoned.

[30] Foreign Application Priority Data

Oct. 12, 1992 [FR] France .................... 92 12123

[51] Int. Cl.$^6$ ............... C07D 417/12; A61K 31/425
[52] U.S. Cl. ............... 514/369; 514/255; 514/326; 514/342; 544/405; 546/209; 546/280; 548/181; 548/183
[58] Field of Search ............... 548/183, 181; 544/405; 546/209, 280; 514/364, 255, 321, 342

[56] References Cited

U.S. PATENT DOCUMENTS 4,330,998  7/1994  Clark .................... 314/369

FOREIGN PATENT DOCUMENTS 9207829  5/1992  WIPO .................... 548/183

OTHER PUBLICATIONS

SOHDA Chem. Pharm Bull 30–3580 (1982).

*Primary Examiner*—Robert Gerstl
*Attorney, Agent, or Firm*—Gordon W. Hueschen

[57] ABSTRACT

The compounds are 5-(4-substituted benzyl)thiazolidine-2,4-diones, enantiomers, diastereoisomers and pharmaceutically tolerable salts thereof, useful for treating conditions of insulin-resistance and/or non insulin-dependent diabetes.

A compound disclosed is: .(R,S)-5-{4-[2-benzofuran-2-yl)carbonylamino)ethyl]benzyl}thiazolidine-2,4-dione.

4 Claims, No Drawings

THIAZOLIDINEDIONE COMPOUNDS

This application is a continuation-in-part of the application Ser. No. 08/133,898 filed Oct. 12, 1993, now abandoned.

The present invention relates to new thiazolidinedione compounds, a process for their preparation and pharmaceutical compositions containing them.

It relates more especially to:

thiazolidinedione compounds of formula I:

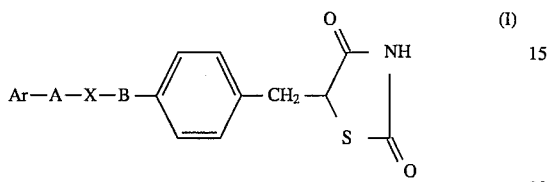

wherein:

Ar represents:

a) a polymethylene ring containing from 5 to 7 carbon atoms which is optionally substituted by one or more alkyl radicals having from 1 to 5 carbon atoms, b) a mono-, bi- or tri-cyclic hydrocarbon radical such as, for example, a phenyl, naphthyl, fluorenyl, dibenzocycloheptenyl or biphenylyl radical, each of which is optionally mono- or poly-substituted by a halogen atom, such as, for example, a fluorine, chlorine or bromine atom, a trifluoromethyl radical, a straight-chain or branched alkyl, alkoxy or alkylthio radical each having from 1 to 5 carbon atoms, an acyloxy radical, a hydroxy radical or a radical of the formula

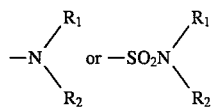

in each of which $R_1$ and $R_2$, which are the same or different, each represents a hydrogen atom, or a straight-chain or branched alkyl radical having from 1 to 5 carbon atoms, or $R_1$ and $R_2$, together with the nitrogen atom to which they are bonded, represent a heterocycle having from 4 to 7 ring members optionally including (in addition to the nitrogen atom) an oxygen or sulphur atom, or c) a mono-, bi- or tri-cyclic heterocyclic radical containing 1 or 2 hereto atoms selected from nitrogen, oxygen and sulphur atoms, such as, for example, a furyl, thienyl, pyrrolinyl, pyridyl, pyrazinyl, oxazolyl, thiazolyl, indolyl, imidazolyl, chromanyl or xanthenyl radical, each of which is optionally substituted by an oxo radical and/or by one or more halogen atoms or alkyl radicals (having from 1 to 5 carbon atoms) or phenyl radicals, each phenyl radical itself optionally being substituted by one or more halogen atoms or trifluoromethyl radicals or alkyl or alkoxy radicals each having from 1 to 5 carbon atoms;

A represents: a single bond, a hydrocarbon chain having 2 or 3 carbon atoms and including a double bond, or a chain of the formula —$(CH_2)_m$—,

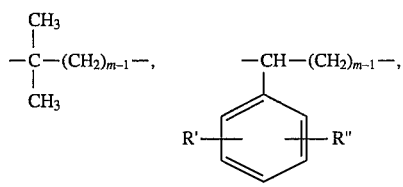

—O—$(CH_2)_m$— or —S—$(CH_2)_m$— wherein:

m is an integer from 1 to 3 and R' and R", which are the same or different, each represents a hydrogen atom or a straight-chain or branched alkyl radical having from 1 to 5 carbon atoms;

X represents an oxygen atom, —CONR— or —$SO_2$NR— wherein R represents a hydrogen atom or a straight-chain or branched alkyl radical having from 1 to 5 carbon atoms and optionally including a double bond, or, when A represents a single bond and Ar represents a phenyl radical, R may also represent a carbonyl radical bonded to Ar by its free bond such that Ar—A—X together form a phthalimido radical;

B represents a saturated hydrocarbon chain having from 1 to 6 carbon atoms which is optionally branched and/or substituted by a hydroxy radical or an oxo radical;

and also the enantiomers and, when B is branched, the corresponding diastereoisomers.

The prior art is illustrated especially by the patent applications EP 008203, WO 8607056, EP 207581, WO 8504171 and WO 9207850 which relate to thiazolidine-2,4-dione compounds which can be used as antidiabetic agents.

Apart from the fact that the compounds of the present invention are new, they differ from the previously known thiazolidine-2,4-dione compounds in the intensity of their pharmacological properties.

Insulin resistance and the lack of secretion of insulin are responsible for the glucose intolerance observed in patients having non-insulin-dependent diabetes.

The therapeutic agents currently available essentially allow correction of the lack of insulin secretion without necessarily improving the sensitivity to insulin of peripheral tissues (muscles, adipose tissue).

Thiazolidine-2,4-dione compounds are capable of causing a reduction in glycaemia and of improving glucose tolerance in non-insulin-dependent diabetic models without causing an increase in the secretion of insulin.

The compounds of the present invention have the advantage of being especially powerful (more especially compared with ciglitazone, a reference compound belonging to the same chemical class) whilst at the same time not exhibiting harmful haematological effects, as will be demonstrated by the pharmacological study described hereinafter.

The compounds of the present invention may thus be used in the treatment of conditions of insulin resistance and/or of non-insulin-dependent diabetic conditions, making it possible to obtain a better control of glycaemia but with a reduced level of circulating insulin. The prevention of that relative hyperinsulinaemia, associated with a reduction in circulating triglycerides resulting from the action of those compounds, may assist in reducing the risks of macroangiopathy.

The same compounds may furthermore be used in the treatment of hypertension in older patients exhibiting insulin resistance which may or may not be associated with other metabolic anomalies.

The present invention relates also to pharmaceutical compositions comprising as active ingredient a compound of formula I or a physiologically tolerable salt thereof, mixed with or in association with one or more appropriate pharmaceutical excipients.

The pharmaceutical compositions so obtained are generally in dosage form containing from 100 to 200 mg of active ingredient. They may, for example, be in the form of tablets, dragées, gelatin capsules, suppositories or injection or drinkable solutions, and may be administered by the oral, rectal or parenteral route.

The dosage may vary, especially in accordance with the age and weight of the patient, the administration route, the nature of the disorder, and associated treatments, and ranges from 100 to 200 mg of active ingredient from 2 to 3 times per day.

The present invention relates also to a process for the preparation of compounds of formula I characterised in that: either, A) a compound of formula II:

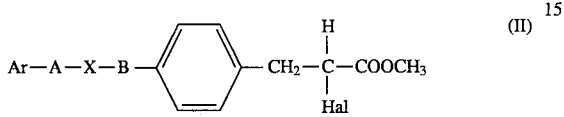

wherein:
Ar, A, X and B are as defined hereinbefore and
Hal represents a chlorine or bromine atom, is reacted with thourea

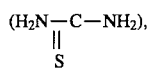

and the imine so obtained of formula III:

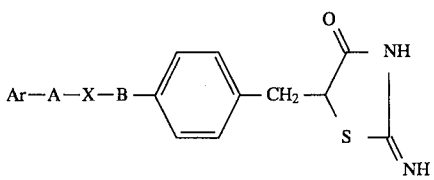

wherein Ar, A, X and B are as defined hereinbefore, is hydrolysed; or,

B) a compound of formula IV:

wherein:
Ar and A are as defined hereinbefore and
X' represents COCl, SO$_2$Cl, an activated ester or —(CO)$_2$O,
is reacted with a compound of formula V:

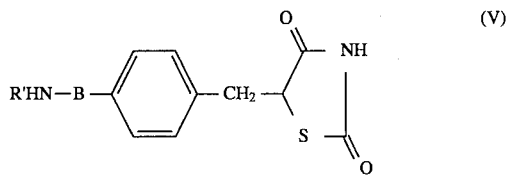

wherein:
B is as defined hereinbefore and
R' represents a hydrogen atom or a straight-chain or branched alkyl radical having from 1 to 5 carbon atoms.

Method A, described by T. Sohda et al, Chem. Pharm. Bull., 30 (10) 3580–3600 (1982), is especially suitable for the preparation of compounds I if carried out in an appropriate solvent such as, for example, methanol, ethanol, sulfolane® or dimethylformamide, heating the mixture of compound II and thiourea at 100°–120° C. for from 6 to 10 hours and then hydrolysing compound III by means of a strong acid, such as HCl or H$_2$SO$_4$.

The starting materials of formula II were prepared from amines of formula:

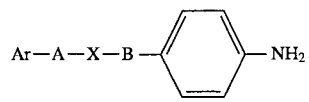

which were themselves obtained by hydrogenating corresponding nitrated compounds under a pressure of 3×10$^5$ Pa in the presence of Raney nickel.

Method B is advantageously carried out by reacting the compounds IV and V at a temperature of 20°–25° C. for from 8 to 15 hours in a suitable solvent, such as, for example, tetrahydrofuran, dimethylformamide or acetonitrile, alone or in the form of a mixture, in the presence of an acceptor for the acid formed during the course of the reaction.

That acceptor may be, for example, triethylamine or an excess of the compound V used for the synthesis. Furthermore, compounds of formula I wherein the group Ar is substituted, inter alia, by a hydroxy radical, may also be prepared by hydrolysing corresponding acyloxy compounds in the presence of sodium hydroxide solution.

Compounds I prepared in accordance with method A or B may be purified by crystallisation from appropriate customary organic solvents or by flash chromatography on an Amicon silica support (35–70μ) using as eluant appropriate solvents such as: CH$_2$Cl$_2$, CH$_2$Cl$_2$/acetone (95:5), toluene/ethanol (95:5), under a pressure of 0.5 to 1 atmosphere of nitrogen.

The compounds of formula I may be converted into addition salts with acids, which salts, as such, form part of the invention. There may be mentioned as acids that can be used for the formation of those salts, for example, in the mineral series, hydrochloric, hydrobromic, nitric, sulphuric and phosphoric acid and, in the organic series, acetic, propionic, maleic, fumaric, tartaric, oxalic, benzoic, methanesulphonic and isethionic acid.

The following Examples illustrate the present invention. Unless specified otherwise, the melting points are determined using a Kofler hot plate.

EXAMPLE 1

5-{4-[2-(2-methoxy-5-chlorobenzamido)ethyl]benzyl}thiazolidine-2,4-dione

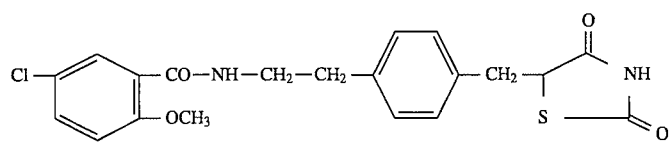

A mixture of 4.1 g of methyl 3-{4-[2-(2-methoxy-5-chlorobenzamido)ethyl]phenyl}-2-chloropropionate (oil) and 1.52 g of thiourea are heated for 10 hours at 120@C in 40 ml of sulfolane®. The imine formed is hydrolysed by adding 14 ml of 2N HCl to the mixture and heating the whole at 100° C. for 8 hours. When the reaction is complete, the whole is diluted with 600 ml of water and the aqueous portion is decanted off. The gummy product is extracted with $CH_2Cl_2$ and the organic solution is washed with water. After evaporation of the solvent, the residue is purified on 90 g of silica by flash chromatography using a mixture of $CH_2Cl_2$ and methanol (95:5) as eluant. The evaporated eluates yield 2.6 g of the desired compound in crystallised form, m.p.: 182° C.

EXAMPLE 2

(R,S)-5-{4-[2-(4-hydroxy-3,5-di-tert-butylbenzamido)ethyl]benzyl}thiazolidine-2,4-dione

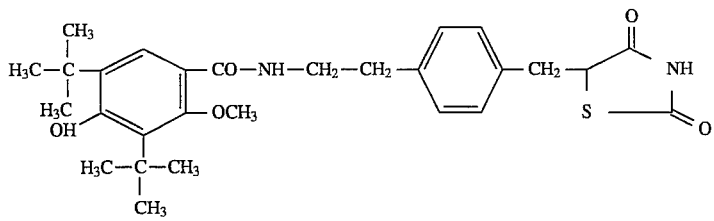

1.9 g of 1,1-carbonyldiimidazole is added to a solution of 3 g of 4-hydroxy-3,5-di-tert-butylbenzoic acid in 150 ml of anhydrous tetrahydrofuran and the solution is stirred at room temperature for 8 hours. 3 g of 5-[4-(2-aminoethyl)benzyl]thiazolidine-2,4-dione (melting at 200° C.) are then added and the mixture is stirred at room temperature for 15 hours. The solvent is then evaporated off and the residue is taken up in a mixture of 10% $Na_2CO_3$ in $CH_2Cl_2$. The precipitate is filtered and then purified by flash chromatography on 180 g of silica using a mixture of $CH_2Cl_2$ and methanol (97:3) as eluant.

After evaporation of the eluates, 3 g of the desired compound in amorphous form are collected. The 5-[4-(2-aminoethyl)benzyl]thiazolidine-2,4-dione starting material was prepared by the method according to SOHDA et al from methyl 3-[4-(2-acetamidoethyl)phenyl]-2-chloropropionate (oil).

EXAMPLE 3

(R,S)-5-{4-[2-(salicyloylamino)ethyl]benzyl}thiazolidine-2,4-dione

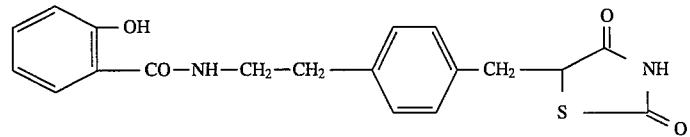

2.3 g of acetylsalicyloyl chloride are added to a solution of 3 g of 5-[4-(2-aminoethyl)benzyl]thiazolidine-2,4-dione and 1.16 g of triethylamine in 50 ml of anhydrous dimethylformamide and the mixture is stirred at room temperature for 15 hours.

The dimethylformamide is then evaporated off and the residue is taken up in $CH_2Cl_2$ and water.

The organic phase is separated off and then evaporated under reduced pressure. 5.3 g of an oily residue are obtained which are chromatographed on 170 g of silica using a mixture of $CH_2Cl_2$ and acetone (90:10) as eluant. Evaporation of the eluates leaves 3 g of amorphous product which is dissolved in 50 ml of ethanol and then hydrolysed in the presence of 8.5 ml of N NaOH at room temperature for 5 hours. The solvent is then evaporated off, the product is taken up in N HCl and the resulting white crystals are suction-filtered.

1.9 g of the desired compound are obtained. M.p.: 184° C.

EXAMPLES 4 TO 51

The following compounds were prepared by operating analogously to the methods described above:

4) 5-{4-[2-(phthalimido)ethyl]benzyl}thiazolidine-2,4-dione, m.p.: 180° C.
5) 5-{4-[2-(diphenylacetylamino)ethyl]benzyl}thiazolidine-2,4-dione, amorphous product.
6) (R,S)-5-{4-[2-(3,3-diphenylpropionamido)ethyl]benzyl} thiazolidine- 2,4-dione, m.p. 148° C.
7) (R,S)-5-{4-[2-(2,5-dimethoxybenzamido)ethyl]benzyl} thiazolidine-2,4 -dione, m.p.: 182° C.
8) (R,S)-5-{4-[2-(4-methoxyphenylsulphamoyl)ethyl] benzyl}thiazolidine-2,4-dione, m.p.: 143° C.
9) (R,S)-5-{ 4-[ 2-(3-trifluoromethylbenzamido)ethyl] benzyl}thiazolidine-2,4-dione, m.p.: 130° C.
10) (R,S)-5-{4-[2-(3,4-dichlorobenzamido)ethyl]benzyl} thiazolidine-2,4-dione, m.p.: 170° C.
11) (R,S)-5-{4-[2-(phenylacetylamino)ethyl]benzyl} thiazolidine-2,4-dione, m.p.: 128° C.
12) (R,S)-5-{4-[2-(phenoxyacetylamino)ethyl]benzyl} thiazolidine-2,4-dione, m.p.: 138° C.
13) (R,S)-5-{4-[2-(cyclopentylcarbonylamino)ethyl] benzyl}thiazolidine-2,4-dione, m.p.: 154° C.
14) (R,S)-5-{4-[2-(fur-2-ylcarbonylamino)ethyl]benzyl} thiazolidine-2,4-dione, m.p.: 150° C.
15) (R, S)-5-{4-[2-(5-methyl-1,2-oxazol-3-ylcarbonylamino)ethyl] benzyl}thiazolidine-2,4-dione, m.p.: 148° C.
16) (R,S)-5-{4-[2-(2-hydroxy-5-chlorobenzamido)ethyl] benzyl}thiazolidine-2,4-dione, m.p.: 242°–244° C.

17) (R,S)-5-{4-[2-(2-amino-5-chlorobenzamido)ethyl] benzyl}thiazolidine-2,4-dione, m.p. (cap): 196°–200° C.
18) (R,S)-5-{4-[2-(2-dimethylamino-5-chlorobenzamido) ethyl]benzyl}thiazolidine-2,4-dione, m.p. (cap): 162°–164° C.
19) (R,S)-5-{ 4-[ 2-(5-methoxyindol-2-ylcarbonylamino)-ethyl]benzyl}thiazolidine-2,4-dione, m.p.: 232°–236° C.
20) (R,S)-5-{4-[2-(pyrid-3-ylcarbonylamino)ethyl]benzyl} thiazolidine-2,4-dione, m.p. (cap): 238°–240° C.
21) (R,S)-5-{4-[2-(pyrid-4-ylcarbonylamino)ethyl]benzyl} thiazolidine-2,4-dione, m.p. (cap): 278°–280° C.
22) (R,S)-5-{4-[2-(cinnamylcarbonylamino)ethyl]benzyl} thiazolidine-2,4-dione, m.p. (cap): 76°–78° C.
23) (R,S)-5-{4-[2-(3-phenylthiopropionamido)ethyl] benzyl}thiazolidine-2,4-dione, m.p. (cap): 76°–78° C.
24) (R,S)-5-{4-[ (R,S)-2-(2,5,7,8-tetramethyl-6 -hydroxy-chroman-2-ylcarbonylamino)ethyl]benzyl}thiazolidine-2,4-dione, amorphous product.
25) (R,S)-5-{4-[2-(pyrazin-2-ylcarbonylamino)ethyl] benzyl}thiazolidine-2,4-dione, m.p.: 198°–200° C.
26) (R,S)-5-{4-[2-(pyrid-2-ylcarbonylamino)ethyl]benzyl} thiazolidine-2,4-dione, m.p.: 160° C.
27) (R,S)-5-{4-[2-(indol-2-ylcarbonylamino)ethyl]benzyl} thiazolidine-2,4-dione, m.p.: 256° C.
28) (R,S)-5-{4-[2-(2-dimethylaminobenzamido)ethyl] benzyl}thiazolidine-2,4-dione, m.p.: 180° C.
29) (R,S)-5-{4-[2-(2-piperidino-5-chlorobenzamido)ethyl] benzyl}thiazolidine-2,4-dione, m.p.: 164°–166° C.
30) (R,S)-5-{4-[ 2-(fur-3-ylcarbonylamino)ethyl]benzyl} thiazolidine-2,4-dione, m.p.: 176°–178° C.
31) (R,S)-5-{4-[2-(5-methyl-2-phenyloxazol-4- ylcarbonylamino)ethyl] benzyl}thiazolidine-2,4-dione, m.p. (cap): 178°–180° C.
32) (R,S)-5-{ 4-[ 2-(5-methyl-2-phenyloxazol-4-ylacetylamino)ethyl]benzyl}thiazolidine-2,4-dione, m.p. (cap): 146°–150° C.
33) (R,S)-5-{4-[3-(2-methoxy-5-chlorobenzamido)propyl] benzyl}thiazolidine-2,4-dione, m.p. (cap): 142° C.
34) (R,S)-5-{4-[2-(2-methoxy-5-trifluoromethylbenzamido)ethyl] benzyl}thiazolidine-2,4-dione, m.p. (cap) with decomposition >160° C.
35) (R,S)-5-{4-[2-(thien-2-ylcarbonylamino)ethyl] benzyl}thiazolidine-2,4-dione, m.p. (cap): 150°–152° C.
36) (R,S)-5-{4-[(5-chloro-2-methoxybenzamido)methyl] benzyl}thiazolidine-2,4-dione, m.p. (cap): 150°–152° C.
37) (R,S)-5-{4-[2-(5-chloro-2-methoxyphenylacetamido)ethyl] benzyl}thiazolidine-2,4-dione, m.p. (cap): 116°–118° C.
38) (R,S)-5-{4-[2-(4-amino-5-chloro-2- methoxybenzamido)ethyl]benzyl}thiazolidine-2,4-dione, m.p. (cap) of the corresponding hydrochloride: 125°–130° C.
39) (R,S)-5-{4-[1-oxo-2-(5-chloro-2- methoxybenzamido)-ethyl]benzyl}thiazolidine-2,4-dione, m.p. (cap): 190°–192° C.
40) (R,S)-5-{4-[1-hydroxy-2-(5-chloro-2- methoxybenzamido)ethyl] benzyl}thiazolidine-2,4-dione, m.p. (cap): 175°–178° C.
41) (R,S)-5-{4-[2-(3,5-di-tert-butyl-4-hydroxyphenoxy)-ethyl]benzyl}thiazolidine-2,4-dione, m.p. (cap): 118°–120° C.
42) (R,S)-5-{4-[2-(3-ethyl-4-methyl-2-oxo-3-pyrrolin-1 -yl-carbonylamino)ethyl]benzyl}thiazolidine-2,4-dione, m.p. (cap): 178°–180° C.
43) (R,S)-5-{4-[2-(3-(3,4-dimethoxyphenyl)prop-2- enoylamino)ethyl]benzyl}thiazolidine-2,4-dione, m.p. (cap): 178°–180° C.
44) (R,S)-5-{4-[2-(3-(3,4-methylenedioxyphenyl)prop-2-enoylamino)ethyl]benzyl}thiazolidine-2,4-dione, m.p. (cap): 155°–157° C.
45) (R,S)-5-{4-[2-(xanthen-9-ylcarbonylamino)ethyl] benzyl}thiazolidine-2,4-dione, m.p. (cap): 138°–140° C.
46) (R,S)-5-{4-[2-(2,2-(2,6-dimethylphenyl)acetylamino) ethyl]benzyl}thiazolidine-2,4-dione, m.p.: 182° C.
47) (R,S)-5-{4-[2-(10,11-dihydro-5H-dibenzo[a,d]cyclohepten-5 -ylcarbonylamino)ethyl]benzyl}thiazolidine-2,4-dione, m.p. (cap): 180°–182° C.
48) (R,S)-5-{4-[2-(3-(4-hydroxy-3-methoxyphenyl)prop-2 -enoylamino)ethyl](benzyl}thiazolidine-2,4-dione, m.p. (cap): 172°–176° C.
49) (R,S)-5-{4-[2-(fluoren-9-ylcarbonylamino)ethyl] benzyl}thiazolidine-2,4-dione, m.p. (cap): 180°–184° C.
50) (R,S)-5-{4-[2-(3-(4-acetoxy-3-methoxyphenyl)prop-2 -enoylamino)ethyl]benzyl}thiazolidine-2,4-dione, m.p. (cap): 135°–140° C.

EXAMPLE 51

(R,S)-5-{4-[2-benzofuran-2-yl carbonylamino)ethyl]benzyl}thiazolidine-2,4-dione

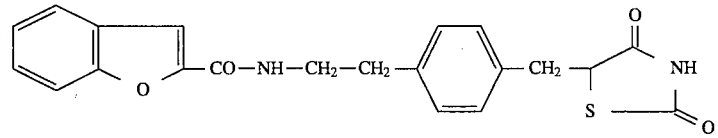

3.25 g (0.02 mole) of 2-benzofuryl carboxylic acid, 5 g of (R,S)-5-[4-(2-amino ethyl)benzyl]thiazolidine-2,4-dione, 100 ml of dimethylformamide and 11.5 g of N-ethylmorpholine are mixed in a three necked flask. Then, the mixture is cooled to 5° C. and a solution at 50% of 17.8 g of 1-propane phosphonic acid anhydride in $CH_2Cl_2$ is added in 30 minutes. The reaction mixture is stirred at 5° C. for 2 hours then at room temperature for 20 hours, then concentrated to dryness. The residue is taken off in $CH_2Cl_2$. The solution is washed with a N-solution of HCl then with water and with a saturated solution of $Na_2CO_3$; then dried over sodium sulfate and concentrated to dryness. The residue is triturated in a mixture of isopropylic ether and ethanol (about 90/10). A crystallisation is observed. The crystals are suction-filtered, washed with isopropylic ether and dried at 60° C. under a pressure of about 67 Pa.

3.9 g of the desired compound are obtained. m.p. (cap): 162°– 164° C., Yield: 49%.

EXAMPLE 52

PHARMACOLOGICAL STUDY

A/ Study of the activity of the compounds of the invention on a non insulin-dependent diabetic model (NIDDM)

The animals (ob/ob mice) are treated each day, for 4 days, by the oral administration of the compounds of the invention suspended in a 20% Senegal gum solution.

Before and after treatment, that is to say on d0 and on d5, blood is taken by piercing the orbital sinus and the glycaemia is determined.

Table 1 shows the doses of the different compounds that need to be administered to obtain the same hypoglycaemic effect (base 100).

TABLE 1

Doses causing the same hypoglycaemic effect in ob/ob mice

| Compounds | Dose mg/kg/day for 4 days | Hypoglycaemic activity |
|---|---|---|
| Ciglitazone | 50–100 | 100 |
| Example 1 | ≦10 | 100 |
| Example 3 | 25 | 100 |
| Example 4 | 10 | 100 |
| Example 6 | 10 | 100 |
| Example 7 | 25 | 100 |
| Example 14 | 10 | 100 |
| Example 15 | 25 | 100 |
| Example 25 | 10 | 100 |
| Example 28 | 10 | 100 |
| Example 33 | 25 | 100 |
| Example 35 | 20 | 100 |
| Example 36 | 20 | 100 |
| Example 40 | 50 | 100 |
| Example 41 | 50 | 100 |
| Example 43 | 25 | 100 |
| Example 44 | 10 | 100 |
| Example 45 | 15 | 100 |
| Example 46 | 40 | 100 |
| Example 51 | 1.1 | 100 |

B/ Study of the activity of the compounds of the invention on a model having reduced glucose tolerance associated with hyperinsulinaemia and hyperlipaemia. The animals (Zucker Fa/Fa male rats) are treated each day, for 10 days, by the oral administration of the compounds of the invention at a dose of 5 mg/kg/day suspended in a 20% Senegal gum solution. On the 11th day the animals are sacrificed and blood is collected in order to determine glycaemia, plasma triglycerides and immuno-reactive insulin. The animals are also weighed before and after treatment.

Under those conditions the compounds of the invention do not have any influence on the level of circulating glucose but decrease the level of triglycerides (TG) and free fatty acids (FFA) in the plasma and also the level of immuno-reactive insulin. The activity is the same as, or superior to, that of other reference thiazolidinedione compounds.

TABLE 2

Pharmacological study of Zucker Fa/Fa male rats

| | Dose (mg/ kg/day for 10 days | Weight ΔP % $d_{11}-d_1$ | Glycaemia (%) | Plasma insulin (%) | TG (%) | AGL (%) |
|---|---|---|---|---|---|---|
| Control | 0 | +100 | 100 | 100 | 100 | 100 |
| Pioglitazone | 5 | +320 | 115 | 49 | 35 | 57 |
| Example 1 | 5 | +112 | 113 | 71 | 94 | 83 |
| Example 4 | 5 | +132 | 108 | 72 | 78 | 108 |
| Example 28 | 5 | +103 | 99 | 75 | 89 | 110 |

Administered per os to male SDCD rats weighing 175 g, contrary to pioglitazone the compounds are without effect on the specified elements of the blood and the plasma volume:

TABLE 3

| Duration of treatment: 8 days | (control values = 100) | | | |
|---|---|---|---|---|
| | White corpuscles | Red corpuscules | Haematocrit | Haemoglobin |
| Pioglitazone: 100 mg/kg/d Example 1: | −46% | −37% | −26% | −29% |
| 100 mg/kg/d | −6% | −2% | +11% | +11% |
| 250 mg/kg/d | −4% | −11% | +4% | +4% |
| Example 51 100 mg/kg/d | 0 | 0 | +2% | +2% |

We claim:

1. A thiazolidinedione compound selected from those of formula I:

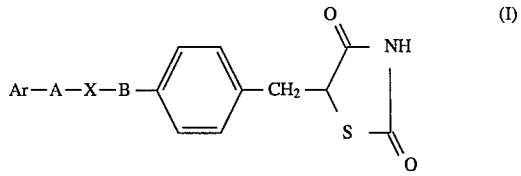

wherein:

Ar represents:
a mono-, bi- or tri-cyclic heterocyclic ring containing besides carbon atoms only 1 or 2 heteroatoms selected from nitrogen, oxygen and sulphur, which is optionally substituted by one oxo and/or by one or more halogen or alkyl (having from 1 to 5 carbon atoms inclusive) or phenyl, itself optionally being substituted by one or more halogen, trifluoromethyl or alkyl or alkoxy each having 1 to 5 carbon atoms inclusive;

A represents: a single bond, or a chain of the formula —(CH$_2$)$_m$— wherein:
m is an integer from 1 to 3 inclusive;

X represents —CONR— or wherein R represents hydrogen or straight-chain or branched (C$_1$–C$_5$) alkyl optionally including a double bond, B represents a saturated (C$_2$–C$_6$) hydrocarbon chain; or its enantiomers or diastereoisomers, as well as its addition salts with a pharmaceutically acceptable acid.

2. A compound of claim 1 which is: (R,S)-5-{4-[2-benzofuran-2-yl)carbonylamino)ethyl] benzyl}thiazolidine-2,4-dione.

3. A pharmaceutical composition, useful for treating conditions of insulin resistance and/or non insulin-dependent diabetes which may or may not be associated with hypertention, comprising as active ingredient an effective amount of at least one compound as claimed in claim 1 together with one or more pharmaceutically-acceptable excipients.

4. A method for treating a mammal afflicted with conditions of insulin resistance and/or non insulin-dependent diabetes which may or may not be associated with hypertension, comprising the step of administering to the said mammal an amount of a compound of claim 1 which is effective for the alleviation of the said condition.

* * * * *

UNITED STATES PATENT AND TRADEMARK OFFICE
CERTIFICATE OF CORRECTION

PATENT NO. : 5,506,245

DATED : April 9, 1996

INVENTOR(S) : Gilbert Regnier, Yves Charton, Jacques Duhault, Joseph Espinal

It is certified that error appears in the above-indentified patent and that said Letters Patent is hereby corrected as shown below:

Title Page, [57] ABSTRACT, line 5: Insert -- ) -- before the dash at the end of the line.

Title Page, [57] ABSTRACT, line 6: Delete ")" at the beginning of the line.

Column 1, line 52: "hereto" should read -- hetero --.

Column 6, line 62: Delete space after "($R$," and continue with text from line 63.

Column 7, line 48: Delete space and continue with text from line 49 after "($R$,".

Column 7, line 56: Delete space and continue with text from line 57 after "($R$,".

Column 8, line 17: Delete space and continue with text from line 18 after "($R$,".

UNITED STATES PATENT AND TRADEMARK OFFICE
CERTIFICATE OF CORRECTION

PATENT NO. : 5,506,245
DATED : April 9, 1996
INVENTOR(S) : Gilbert Regnier, Yves Charton, Jacques Duhault, Joseph Espinal It is certified that error appears in the above-indentified patent and that said Letters Patent is hereby corrected as shown below:

Column 10, line 14: Delete the four (4) numbers in columns 2 thru 5, and move them to line 16.

Column 10, line 42: Delete "from".

Signed and Sealed this

Eighth Day of October, 1996

Attest:

BRUCE LEHMAN

Attesting Officer     Commissioner of Patents and Trademarks